United States Patent [19]

Deleo

[11] Patent Number: 4,935,016
[45] Date of Patent: Jun. 19, 1990

[54] SYRINGE

[76] Inventor: John Deleo, 107 Sun Valley Dr., Southington, Conn. 06489

[21] Appl. No.: 157,369

[22] Filed: Feb. 17, 1988

[51] Int. Cl.$^5$ ............................................. A61M 5/32
[52] U.S. Cl. ..................................... 604/198; 604/263
[58] Field of Search ................ 604/198, 263, 187, 192

[56] References Cited

U.S. PATENT DOCUMENTS 4,737,144  4/1988  Choksi ................................. 604/198

Primary Examiner—John D. Yasko

[57] ABSTRACT

Disclosed is a syringe including a barrel 12 having a needle 14 extending outwardly therefrom and a guard member 22 carried on the barrel, and movable between a retracted position exposing said needle and an extended position covering said needle. The guard member 22 has the ability to expand and contract as it is moved between retracted and extended positions. Interactive locking elements 38, 40, 57 and 59 on the barrel 12 and the guard member 22 permanently lock the guard member in the extended position, with pin elements 38 and 40 engaging the guard member to expand the guard member as it moves between the retracted and extended positions.

8 Claims, 5 Drawing Sheets

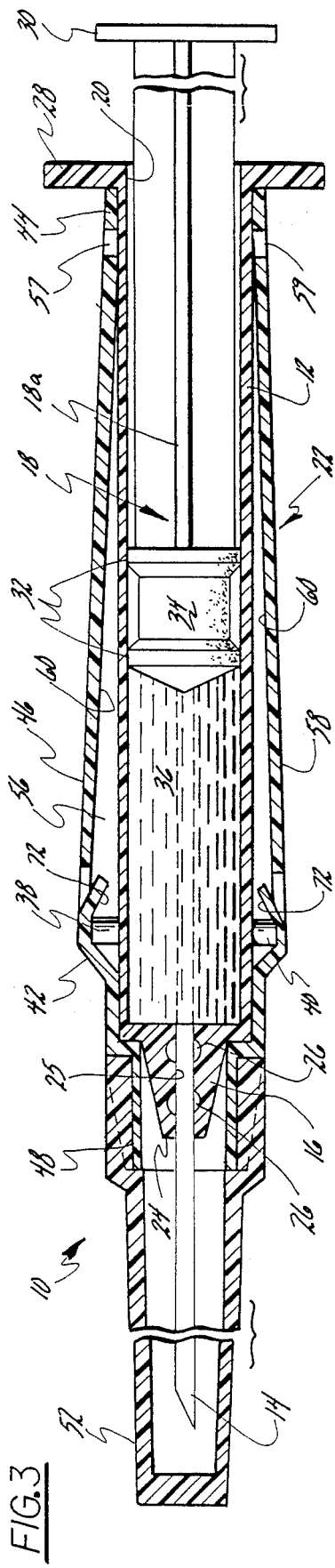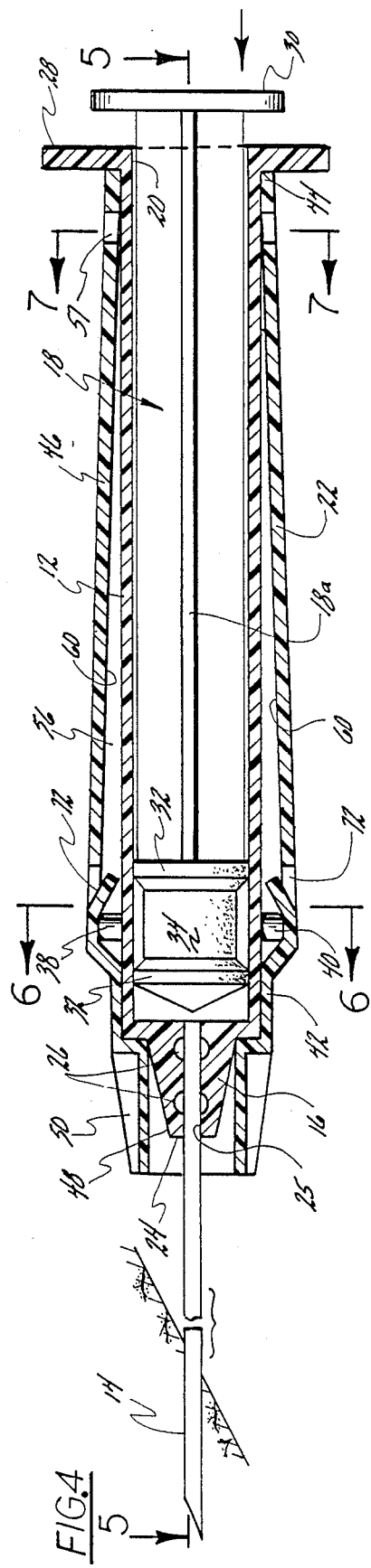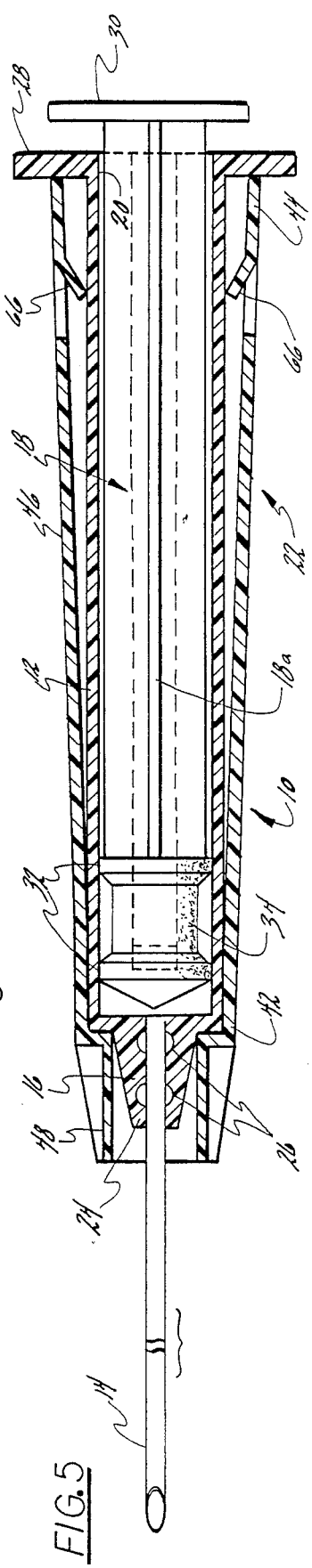

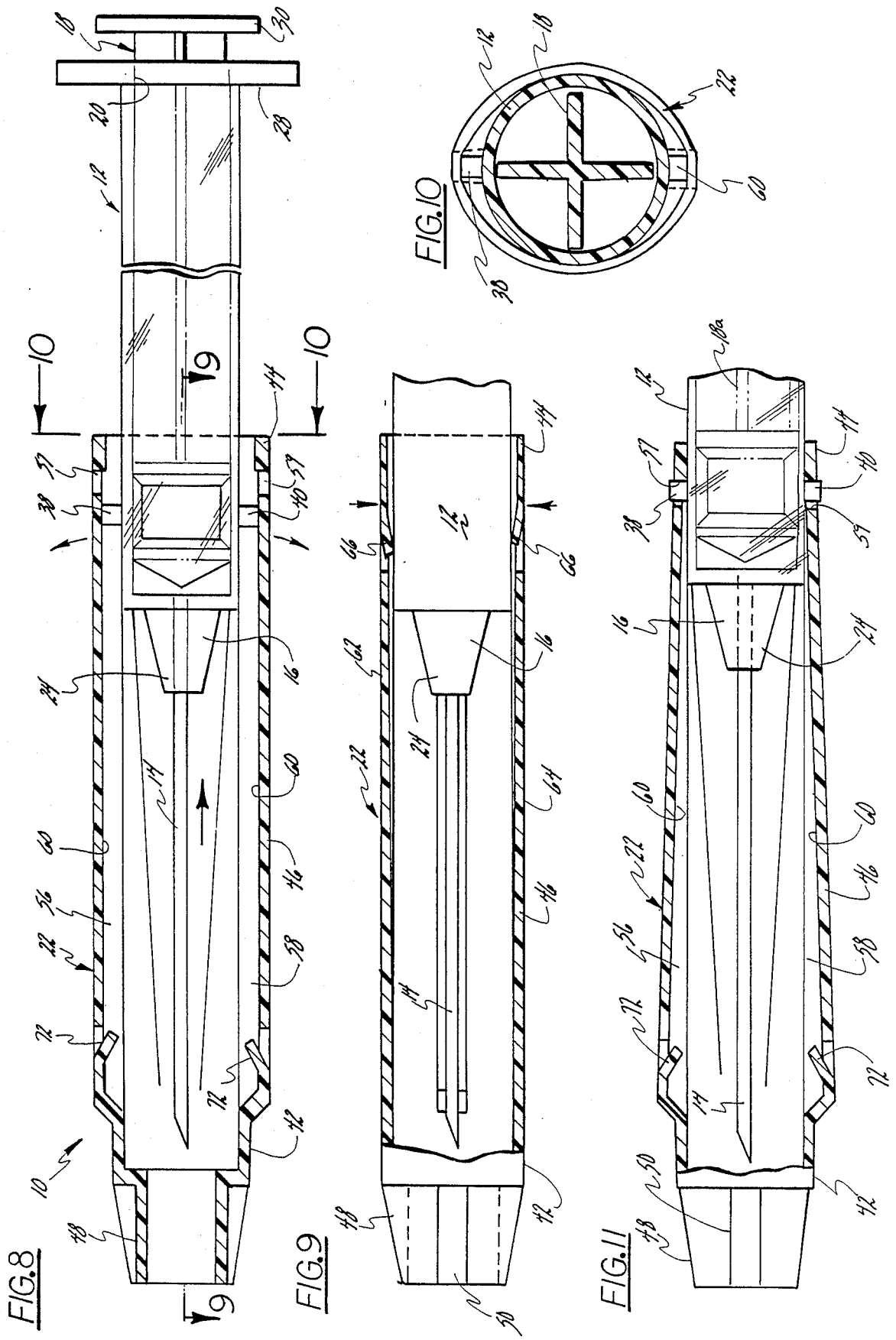

SYRINGE

BACKGROUND OF THE INVENTION

1 Field of the Invention:

This invention relates to syringes, and particularly to a syringe with an expandable guard that protects against accidental needle sticks.

2 Background Discussion:

As disclosed in U.S. Pat. No. 4,631,057, needle guards are used with syringes to protect against accidental needle sticks. These needle guards are mounted on the barrel of the syringe and movable between a retracted position where the tip of the needle extending from the barrel is exposed and an extended position where the guard is manually moved forward to cover the tip of the needle and locked into position.

SUMMARY OF THE INVENTION

The present invention provides a syringe with an expandable needle guard which is interactive with locking elements carried on the syringe barrel to lock the guard in the extended position.

There are several features of this invention contributing to its safety and convenience, no single one of which is solely responsible for these desirable attributes. Without limiting the scope of this invention as expressed by the claims, its more prominent features will now be discussed. After considering this discussion, and particularly after reading the section of this application entitled DETAILED DESCRIPTION OF THE PREFERRED EMBODIMENTS, one will understand how the features of this invention provide for the attributes of safety and convenience.

One feature of this invention is the use of a guard member that has at one end an oval configuration and at its opposed end a circular configuration. A pair of guideways are provided in the guard member which are interactive with locking pins mounted on the syringe barrel. The pins ride along the guideways to expand the guard member outwardly at its oval end. There are openings in the barrel near the oval end which receive the pins when the pins are in registration with these openings. The guard member is made of a flexible resilient material such as polypropylene, which will provide internal spring action to enable the guard member to snap back into its original shape after being expanded outwardly by the pins.

The second feature of this invention is the use of guide fingers to align the syringe barrel in the guard member and enable the guard member to move with a single action between the retracted and extended positions. These guide fingers are integral with the sidewall of the guard member.

The third feature of this invention is the use of a retaining member, such as an annular ring on the inside of the guard member which engages the pins and holds the guard member in the retracted position when an injection is being given, but enables the user to override the retainer member by simply manually moving the guard forward over the tip of the needle.

The fourth feature of this invention is the use of a cap element to cover the tip of the needle after an injection has been given.

BRIEF DESCRIPTION OF THE DRAWING

Several embodiments of this invention illustrating all of its feature will now be discussed in detail in connection with the accompanying drawing, wherein like numerals indicate like parts, and in which:

FIG. 3 is a cross-sectional view taken along line 3—3 of FIG. 1.

FIG. 4 is a cross-sectional view, similar to that shown in FIG. 3, with the needle inserted into the body of a patient and the plunger of the syringe depressed to inject medication through the needle into the patient.

FIG. 5 is a cross-sectional view taken along line 5—5 of FIG. 4.

FIG. 8 is a side elevational view, partially in cross section, showing the guard member being moved into the extended position.

FIG. 9 is a cross-sectional view taken along line 9—9 of FIG. 8.

FIG. 10 is a cross-sectional view taken along line 10—10 of FIG. 8.

FIG. 11 is a fragmentary view, partially in section, showing the guard member in the extended position with the pins received in the openings in the guard member.

DESCRIPTION OF THE PREFERRED EMBODIMENTS

Figure 1:
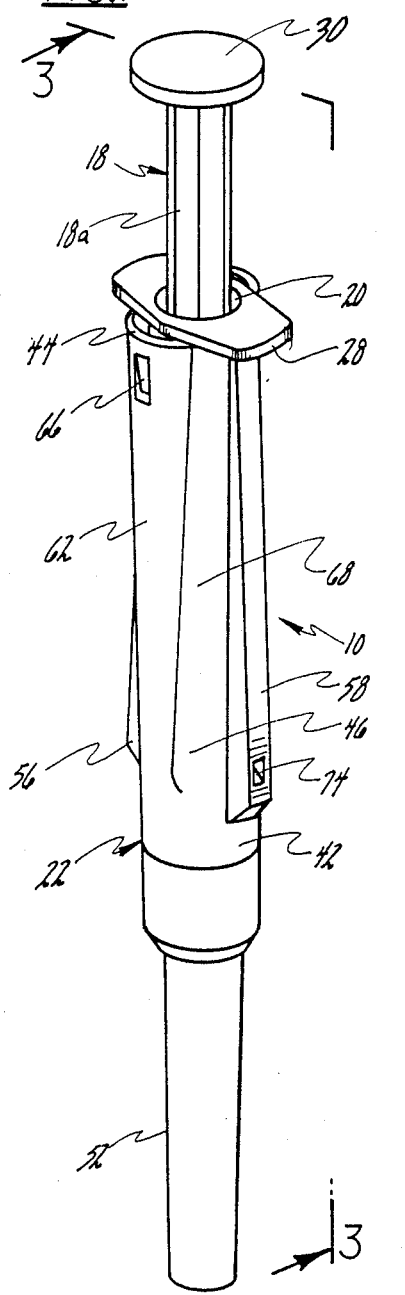
FIG. 1 is a perspective view of the syringe of this invention.
Figure 2:
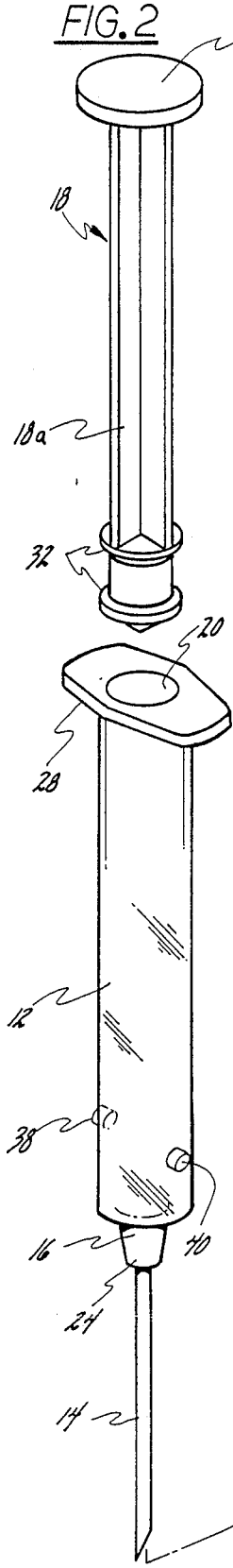
FIG. 2 is an exploded perspective view of the syringe shown in FIG. 1.
Figure 6:
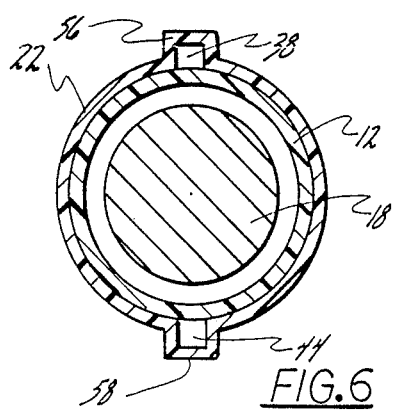
FIG. 6 is a cross-sectional view taken along line 6—6 of FIG. 4.

As best shown in FIGS. 1 and 2, the syringe 10 of this invention includes a transparent syringe barrel 12 having a hollow needle 14 projecting outwardly from the closed end 16, a plunger 18 which fits into the open end 20 of the syringe barrel, and an expandable guard member 22 carried by the syringe barrel.

The syringe barrel 12 is made of any suitable plastic material, such as polypropylene, and has a generally hollow, cylindrical configuration with a needle mount 24 carried at the closed end 16 of the barrel from which the needle extends outwardly. The needle mount 24 may include, for example, a passageway 25 (FIG. 3) having a pair of internal annular recesses 26 in the passageway wall which receive an adhesive for gluing the needle securely in position in the needle mount. The open end 20 of the syringe barrel 12 has an outwardly projecting flange 28 surrounding the open end. As best shown in FIGS. 2, 3 and 4, a pair of diametrically opposed pins 38 and 40 extend outwardly from the exterior surface of the syringe barrel. These pins 38 and 40 are adjacent the end of the barrel carrying the needle and are interactive with the guard member 22 to enable the guard member to be moved to an extended position as shown in FIG. 11 from the retracted position shown in FIG. 4.

The plunger 18 is of conventional design and has a body 18a of general cross shape with a circular depressor plate 30 integral with the body of the plunger. At the end of the plunger inserted into the interior of the syringe barrel 12 are a pair of annular rubber seals 32 which surround a generally depressed section 34 in the end of the plunger body 18a. The diameter of the plunger body 18a is such that the rubber seals will fit snug against the interior wall of the barrel 12 and provide a seal so that the fluid retained in the barrel will not escape past the seals.

The guard member 22 has a generally hollow cylindrical configuration and is made of a resilient polymeric material such as polypropylene. As will be apparent from the subsequent discussion, this enables the guard member 22 to expand and change shape as it moves from the retracted to the extended position, and then spring back to its normal shape as shown in FIG. 2 upon reaching the fully extended position.

The guard member 22 has a generally circular end 42 and, opposed to this circular end, is a generally oval end 44 with an annular wall 46 connecting these two ends. A nose section 48 is provided which extends outwardly from the circular end 42. This nose section 48 has four ribs 50 equally spaced apart which, when the nose is inserted into a cover 52, coact with splines 54 in the cover to firmly seat the cover on the nose section as shown in FIG. 1.

Figure 7:
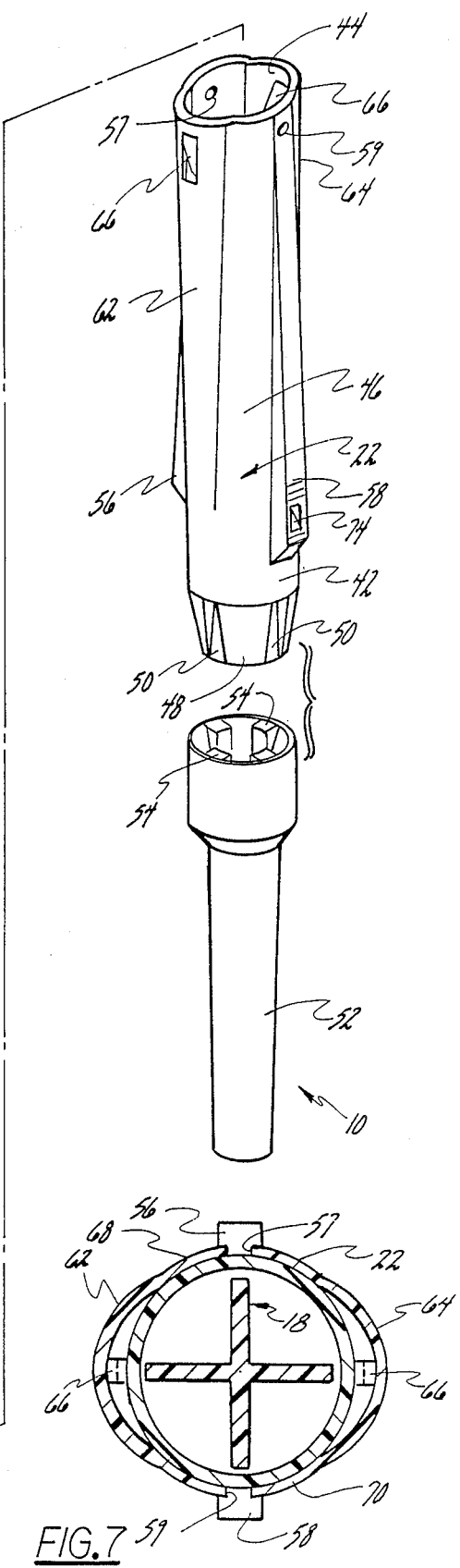
FIG. 7 is a cross-sectional view taken along line 7—7 of FIG. 4.
Figure 12:
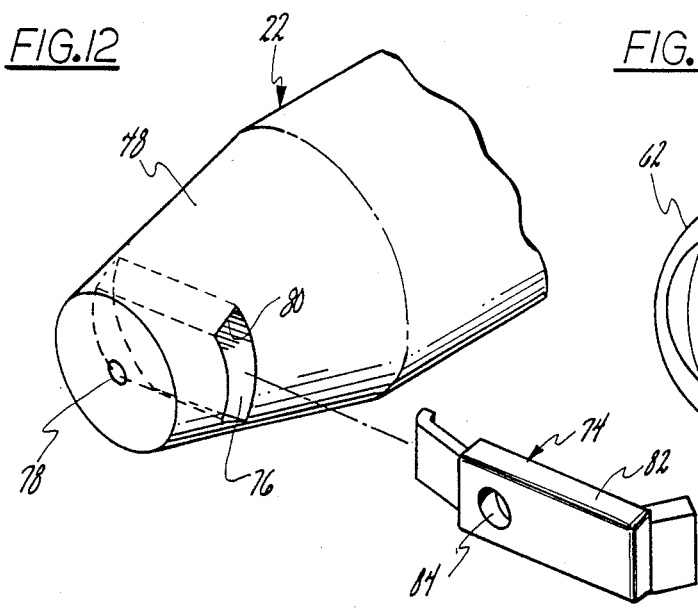
FIG. 12 is a perspective view showing an alternate embodiment of this invention employing a cap to close off the end of the syringe after the guard member has been moved to the extended position.
Figure 13:
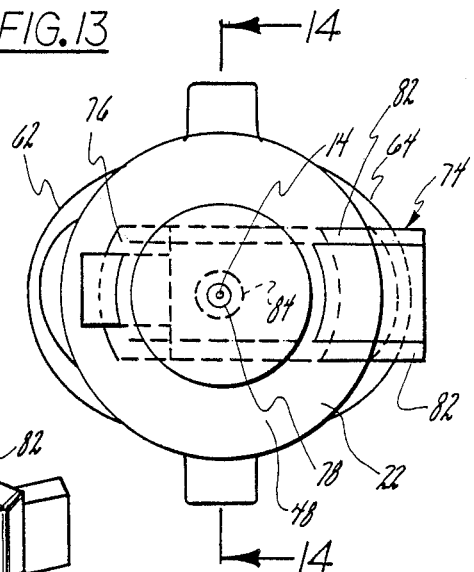
FIG. 13 is a front elevational view of the syringe shown in FIG. 12.
Figure 14:
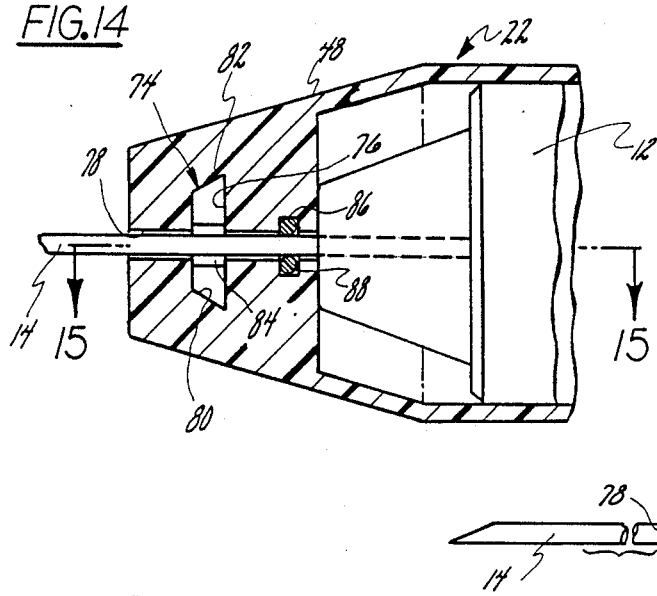
FIG. 14 is a cross-sectional view taken along line 14—14 of FIG. 13.
Figure 15:
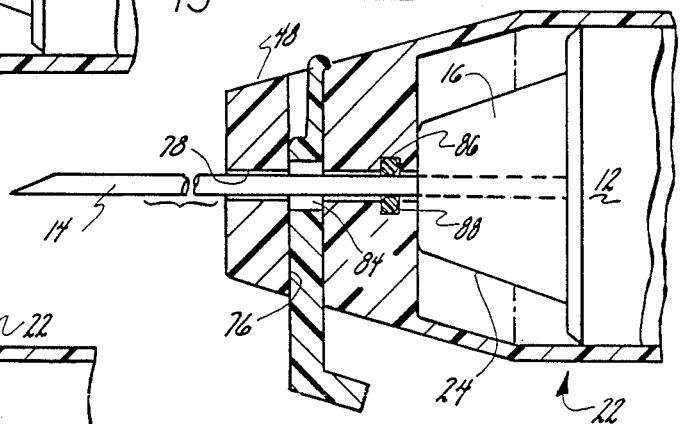
FIG. 15 is a cross-sectional view taken along line 15—15 of FIG. 14.
Figure 16:
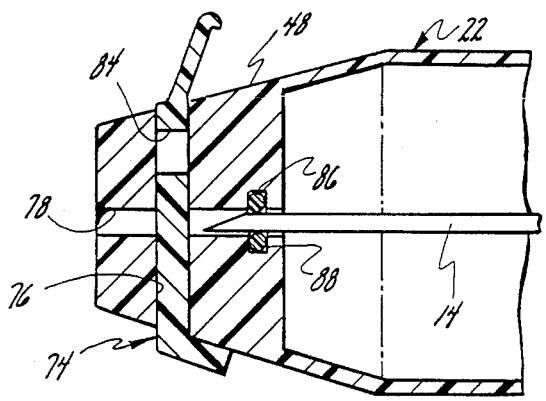
FIG. 16 is a cross-sectional view similar to that shown in FIG. 15 showing the guard member in the extended position and the cap closing off the end of the syringe.
Figure 17:
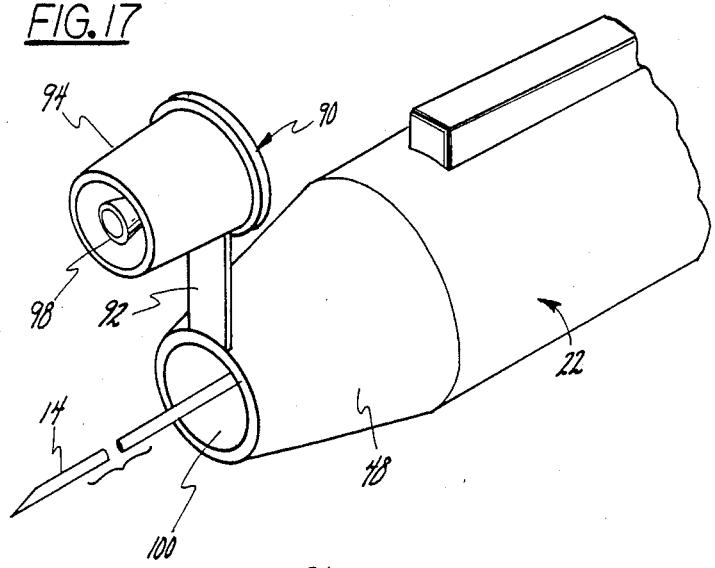
FIG. 17 is a perspective view of another alternate embodiment of the syringe of this invention.
Figure 18:
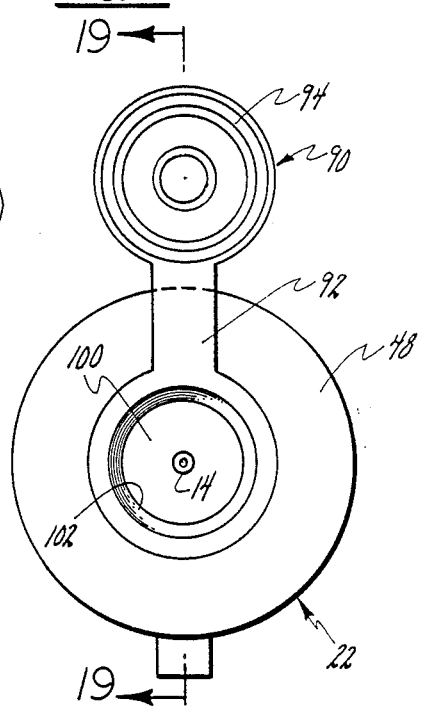
FIG. 18 is a front elevational view of the syringe shown in FIG. 17.
Figure 19:
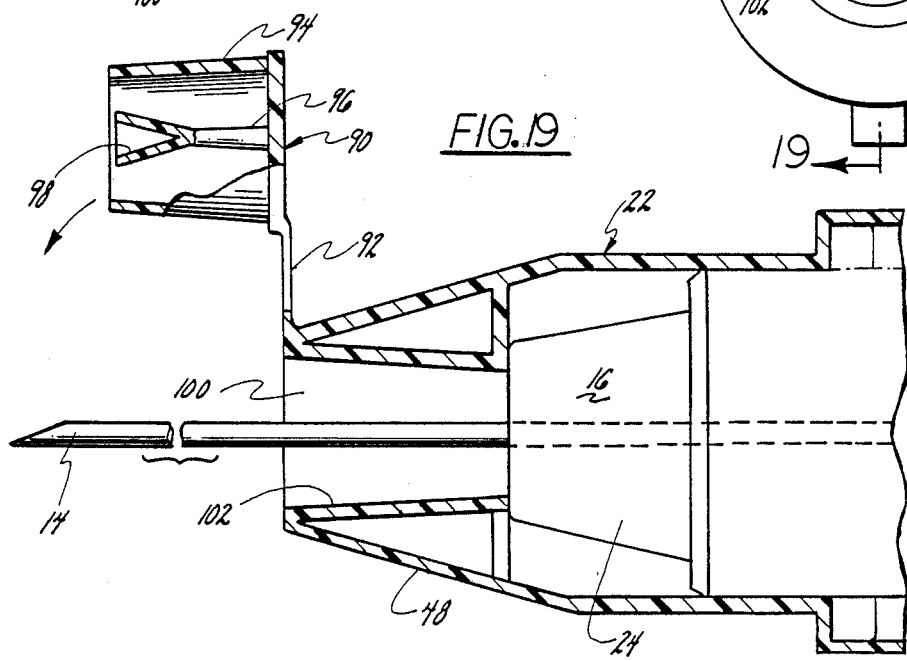
FIG. 19 is a cross-sectional view taken along line 19—19 of FIG. 18.
Figure 20:
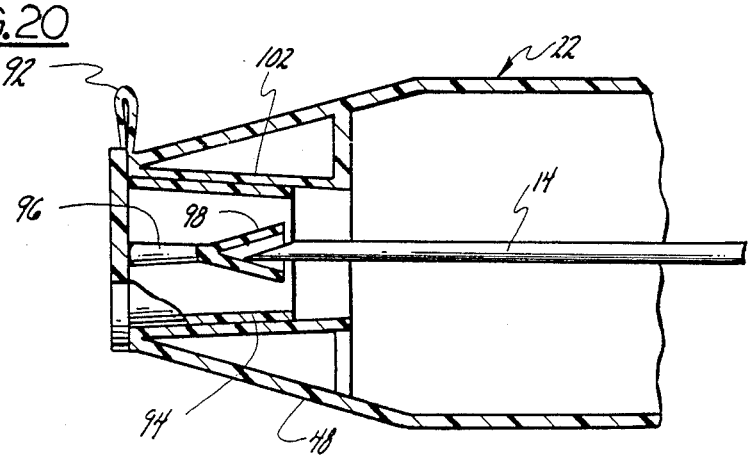
FIG. 20 is a cross-sectional view similar to that shown in FIG. 19 showing the guard member in the extended position and the cap in position closing off the end of the syringe.

The wall 46 has two generally opposed guideways 56 and 58 therein which form internal tracks along which the pins 38 and 40, respectively, ride. At the end of each guideway is an opening 57 and 59, respectively, and each guideway has a inwardly tapering inside wall 60 (FIGS. 3, 4, 8 and 11), with the end of each pin 38 and 40 engaging this wall. The wall 46 has two opposed outwardly tapering sections 62 and 64 which terminate in the oval end 44. In each of these curved sections 62 and 64 is a guide finger 66 which extends inwardly towards and rests against the exterior surface of the syringe barrel 12 as shown in FIGS. 5 and 9. The wall sections 68 and 70 in which the guideways 56 and 58 are formed have a generally circular cross-section and, as shown in FIG. 7, will have a diameter slightly greater than the diameter of the syringe barrel 12 to enable the syringe barrel to move laterally and be guided by these circular wall sections.

Because of the unique configuration of the guard member 22, upon movement of the guard member from the retracted position (FIG. 7) to the extended position (FIG. 8), the oval end of the guard member simultaneously expands outwardly adjacent the openings 57 and 59 and contracts inwardly at the fingers 66 as shown in FIG. 10. As this occurs, the fingers 66, which are biased inwardly, are pressed outwardly by the exterior wall of the syringe barrel as shown in FIG. 9. When the pins 38 and 40 are opposite the openings 57 and 59 in the guard member 22, the oval end 44 returns to its normal configuration shown in FIG. 7 and the pins pop through the opening to permanently lock the guard member in the extended position. Thus, because of the inherent spring bias of the wall 46, the guard member 22 expands as the guard member moves from the retracted into he extended position, but snaps back to its original shape when the pins 38 and 40 are in registration with the openings 57 and 58. As shown in FIG. 3, the internal wall of the guard member 22 near the circular end 42, has stops 72 therein. These stops 72 are similar in construction to fingers 66, and will hold the guard member 22 in the retracted position until manually overridden.

The guard member 22 is configured to grip the barrel 12 firmly with the guard member in the retracted position. Normally, there is sufficient forced exerted by the guard member 22 on the barrel 12 to prevent the guard member from moving laterally along the barrel. As a precautionary measure, the stops 72 are also used to prevent unwanted lateral movement of the guard member 22. As shown in FIG. 3, the stops 72 abut the pins 38 and 40 when the guard member 22 is in the retracted position. The stops 72 thus hold the guard member 22 in the retracted position while the user is inserting the needle tip into the body of the patient. When the user pushes the guard member forward, the pins 38 and 40 simply deflect the stops 72 inwardly, there being sufficient elasticity in the stops to deform and then spring back to their original condition. There is sufficient strength, however, provided by the stops 72 to prevent the guard member 22 from simply moving forward without being actually forced to deflect the stops inwardly by the user. Moreover, force is required to expand the guard member 22 outwardly, thus the guard member normally tends to stay in the retracted position unless it is manually forced forward to the extended position. The guideways 56 and 58 may also have small slits 74 therein that provide for expansion to facilitate moving the pins 38 and 40 past the stops 72.

OPERATION

To use the syringe 10 of this invention, the cover 52 is first removed and then the user grasps the syringe using the thumb to press against the depression plate 30 of the plunger 18 and the index and middle finger to hold the flange 28. The tip of the needle 14 is inserted into the body of a patient as shown in FIG. 4 and the plunger 18 is manually depressed to expel the fluid 36 carried in the barrel 12 out the needle tip.

The user, with the hand not being used to hold the syringe 10, grasps the guard member 22, preferably adjacent the circular end 42 of the guard member, and then pulls rearwardly with the hand holding the flange 28. This pulls the syringe barrel 12 out the oval end 44 of the guard member 22 as shown in FIG. 8. As the syringe barrel 12 advances towards the oval end 44, the pins 38 and 40 first ride over the stops 72 and then ride along the track in the guideways 56 and 58. By pulling rearwardly on the flange 28, the pins 38 and 40 push against the interior surface of the wall 60 of the guideway to force the guard member to change shape as illustrated in FIGS. 8 and 10. When the pins 38 and 40 are immediately adjacent the openings 57 and 59 as shown in FIG. 8, the guard member 22 has been expanded outwardly in the direction of the openings fully as illustrated in FIG. 10. By continuing to move rearwardly, the pins 38 and 40 move into alignment with the openings 57 and 59 in the guard member 22. At this point, the guard member will contract immediately, to snap the pins 38 and 40, respectively, into the openings 57 and 59 as shown in FIG. 11. The guard member 22 is now permanently locked in an extended position, covering the tip of the needle 14 which has been withdrawn into the interior of the guard member 22 as the user pulls rearwardly on the syringe barrel 12. The user will now cover the tip of the needle by replacing the cover 52, fitting it over the nose section 48 of the guard member 22 with the ribs 50 interlocking with the splines 54.

ALTERNATE EMBODIMENTS

FIGS. 12 through 16 illustrate an alternate embodiment of this invention wherein the nose section 48 of the guard member 22 is equipped with a slidable cap element 74 which is received in a slot 76 in the nose section 48. The nose section 48 has a central longitudinal opening 78 through which the needle 14 extends. The slot 76 is generally at right angles with respect to the opening 78 and has beveled sidewalls 80 which fit snug with the beveled sidewalls 82 of the cap element 74. This cap element 74 has an opening 84 therein through which the needle 14 extends. In the nose section 48 rearwardly from the slot 76 is a recess 86 retaining an O-ring seal 88 which fits snug around the circumference of the needle 14. When the guard member 22 is in the retracted position the needle passes through the opening 84 in the cap element 74. On movement of the guard member 22 to the extended position, the needle 14 is withdrawn inwardly past the slot 76. At this point the cap element 74 is pushed inwardly (FIG. 16) to close off the opening 78, retaining the tip of the needle 14 between the cap element 74 and O-ring seal 88. Thus, any blood on the needle 14 is wiped off by the O-ring seal 88 as the guard member 22 moves forward and retained in the space between the cap element 74 and the O-seal.

The third embodiment of this invention is shown in FIGS. 17 through 20. It includes a cap element 90 mounted on the nose section 48 of the guard member 22 by a strip 92 of plastic which is integral with the cap element 90 and the guard member 22. The cap element 90 includes a generally inwardly tapered conical sidewall 94 with a centrally located post 96 having a funnel-like section 98. Upon moving the guard member 22 to the extended position, the cap element 90 is folded inwardly and forced into the open end 100 of the guard member. This open end 100 has an inwardly tapered conical sidewall 102 which receives the truncated conical cap element 90. The tip of the needle 14 fits into the funnel section 98. Closure of the cap element 90 thus closes off the open end 100 of the guard member 22 to prevent blood from escaping the syringe.

SCOPE OF THE INVENTION

The above description presents the best mode contemplated of carrying out the present invention as depicted by the three embodiments disclosed. The combination of features illustrated by these embodiments provide the safety and convenience of this invention. This invention is, however, susceptible to modifications and alternate constructions from the embodiments shown and described above. Consequently, it is not the intention to limit it to the particular embodiments disclosed. On the contrary, the intention is to cover all modifications and alternate constructions falling within the scope of the invention as generally expressed by the following claims.

I claim:
1. A syringe including
a barrel element having a needle extending outwardly from an end of the barrel element,
a pair of outwardly projecting, diametrically opposed, pins mounted on the exterior of the barrel element adjacent said end,
an expandable guard member carried by the barrel, said guard member having a first end of a generally circular configuration, a second end opposed to said first end having a generally oval configuration, and a wall member joining said first and second ends,
said wall member having therein a pair of guideways, each guideway being aligned with a pin to enable each pin to travel along its respective guideway, and each guideway including an inwardly tapering wall having a terminal end adjacent the second end of the guard member,
a pair of openings in each of said guideway walls adjacent the terminal end for receiving a pin,
said guard member being mounted to move between a retracted position where the pins are adjacent the first end of the guard member and an extended position covering the needle to protect against accidental needle sticks,
said pins engaging the tapered wall and urging the guard member to expand outwardly as the guard member moves from the retracted position toward the extended position and being received in the openings upon being moved into registration with said openings, with said guard member contracting and the pins permanently locking the guard member in the extended position when the guard member is moved into said extended position.

2. The syringe of claim 1 wherein the guard member has a removable cap element for covering the guard member after the guard member is moved to the extended position.

3. The syringe of claim 2 wherein the cap element is integral with the guard member.

4. The syringe of claim 2 wherein the cap element provides a sealed chamber which captures any blood retained on or in the needle.

5. The syringe of claim 1 wherein the guard member includes guide fingers for guiding the guard member over the barrel as said guard member moves between the retracted and extended positions.

6. A syringe including
a barrel element having a needle extending outwardly from an end thereof,
an expandable guard member carried by the barrel element and movable along the barrel element between a retracted position exposing said needle and an extended position covering the needle to protect against accidental needle sticks,
said guard member being in a contracted condition when in the retracted position and expanding as the guard member moves between the retracted and extended positions, and
interactive locking elements on the barrel element and the expandable guard member which permanently lock the guard member in the extended position, one of said elements engaging the guard member to expand said guard member as it moves between said retracted and extended positions, said interactive locking elements including a pin on the barrel element and an opening in the guard member, with the pin snapping into locking engagement with the opening upon movement of the pin into registration with the hole.

7. A syringe of claim 6 wherein the guard member is made of a material that imparts resiliency to the guard member to enable it to change from its original shape as it moves between the retracted and extended positions and then return to its original shape upon moving to the extended position.

8. A syringe including a barrel element having a needle extending outardly from an end thereof, a guard member having an original predetermined shape and made of a resilient material that enables the guard member to change its shape when a force acts on said guard member and then return to its predetermined shape when the force discontinues to act on said guard member, said guard member being carried by the barrel element and movable along the barrel element between a reacted position exposing the needle and an extended position covering the needle to protect against accidental needle sticks, said guard member in the retracted position gripping the barrel element firmly, means for applying a force on the guard member as it moves between the retracted and extended position to change the shape of the guard member so that said guard member releases its firm grip on the barrel element and slides along the barrel moving between said positions, said means for applying force including a pin element extending outardly from the barrel element that engages the guard member, and means for permanently locking the guard member in the extended position.

* * * * *